United States Patent [19]

Panzeri et al.

[11] Patent Number: 5,719,159
[45] Date of Patent: Feb. 17, 1998

[54] 4-AZASTEROIDS WITH SIDE-CHAIN FLUOROKETONES

[75] Inventors: Achille Panzeri, Merate; Marcella Nesi; Enrico Di Salle, both of Milan, all of Italy

[73] Assignee: Pharmacia S.p.A., Milan, Italy

[21] Appl. No.: 615,242

[22] PCT Filed: Jul. 7, 1995

[86] PCT No.: PCT/EP95/02649

§ 371 Date: May 31, 1996

§ 102(e) Date: May 31, 1996

[87] PCT Pub. No.: WO96/03422

PCT Pub. Date: Feb. 8, 1996

[30] Foreign Application Priority Data

Jul. 28, 1994 [GB] United Kingdom .............. 9415178

[51] Int. Cl.$^6$ ...................... A61K 31/58; C07D 221/02
[52] U.S. Cl. .................................. 514/284; 546/77
[58] Field of Search .................. 546/77; 514/284

[56] References Cited

U.S. PATENT DOCUMENTS

| | | | |
|---|---|---|---|
| 5,155,107 | 10/1992 | Panzeri et al. | 514/232.8 |
| 5,342,948 | 8/1994 | Panzeri et al. | 546/77 |
| 5,407,939 | 4/1995 | Panzeri et al. | 514/284 |
| 5,418,238 | 5/1995 | Panzeri et al. | 514/284 |

FOREIGN PATENT DOCUMENTS 0478066  9/1991  European Pat. Off. .

*Primary Examiner*—Mukund J. Shah
*Assistant Examiner*—King Lit Wong
*Attorney, Agent, or Firm*—Oblon, Spivak, McClelland, Maier, & Neustadt, P.C.

[57] ABSTRACT

The present invention provides compounds of formula (I) wherein the symbol ‐‐‐ represents a single or a double bond; R is a hydrogen atom or a $C_1$–$C_4$ alkyl group; A is a single bond or a straight or branched $C_1$–$C_6$ alkylene chain; B is a straight or branched $C_1$–$C_{12}$ alkylene group optionally substituted by one or more aryl groups or fluorine atoms; W is a group $R_1$ or (a) wherein $R_1$ is a straight or branched $C$–$C_6$ alkyl group unsubstituted or substituted by one or more fluorine atoms, provided that at least a fluorine atom is present in B or W. The compounds of the invention are useful as testosterone 5α-reductase inhibitors.

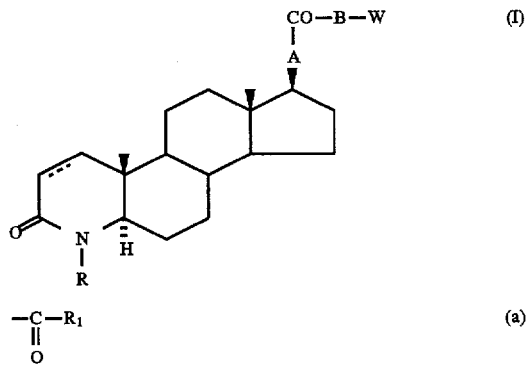

7 Claims, No Drawings

4-AZASTEROIDS WITH SIDE-CHAIN FLUOROKETONES

The present invention relates to novel 4-azasteroids with side-chain fluoroketones, to a process for their preparation, and to pharmaceutical compositions containing them. These compounds are inhibitors of androgen action, by means of testosterone 5α-reductase inhibition.

In certain androgen responsive tissues the action of testosterone is mediated primarily through its 5α-reduced metabolite, dihydrotestosterone (DHT) (Bruchowsky N., Wilson J. D.; J. Biol. Chem. 243, 5953, 1968). The conversion of testosterone to dihydrotestosterone is catalysed by the enzyme 5α-reductase and if 5α-reductase is inhibited, the formation of dihydrotestosterone is reduced and its specific androgenic effect is attenuated or prevented.

The 5α-reductase inhibitors may find medical application for the treatment of hyperandrogenic conditions, e.g. certain prostatic diseases, such as benign prostatic hyperptasia and prostatic cancer, and certain skin-hair conditions, such as acne, seborrhoea, female hirsutism and male pattern baldness (Siiteri P. K., Wilson J. D., J. Clin. Invest. 49. 1737. 1970; Price V. H., Arch. Dermatol. III, 1496, 1975; Sandberg A. A., Urology 17, 34, 1981). Also breast cancer treatment can take advantage from use of 5α-reductase inhibitors as the said tumour is known to be aggravated by presence of androgens. Androst-4-en-3-one-17β-carboxylic acid and its methyl ester (Voigt and Hsia, Endocrinology, 92, 1216 (1973); Canadian Patent No. 970,692) are among the first steroidic compounds described as 5α-reductase inhibitors.

Two 5,10-secosteroids having a 3-keto-4,5-diene system in the expanded ring have been found to be selective inhibitors of rat epididymal 5α-reductase (Robaire et al., J. Steroid Biochem. 8, 307–310 (1977)).

The (20R)-4-diazo-21hydroxy-20-methyl-5α-pregnan-3-one and its analogs are reported to be enzyme activated inhibitors of testosterone 5α-reductase (Blohm et al., Biochem. Biophys. Res. Comm. 95, 273–80 (1980); U.S. Pat. No. 4,317,817). Another series of enzyme-directed irreversible inhibitors of 5α-reductase have been prepared by introducing a 6-methylene moiethy into substrates type 3-keto-D⁴-progestins and androgens (Petrow et al., Steroids 38, 352–53 (1981); U.S. Pat. No. 4,396,615)).

Later on unsaturated derivatives of 3-carboxy steroids have been reported as uncompetitive 5α-reductase inhibitors versus testosterone (Biorg. Chem. 17, 372–376 (1989); Eur. Pat. Appln. No. 0289327; Eur. Pat. Appln. No. 0465123; Eur. Pat. Appln. No. 0528485; Eur. Pat. Appln. No. 0567271).

4-Aza steroids are by far the most studied steroid 5α-reductase inhibitors. The compounds known in the art are reported in a very large number of publications and patents. In particular the 17β-acylamides and their metabolites are described in: J. Med. Chem. 27. 1690–1701 (1984), J. Med. Chem. 29, 2298–2315 (1986), Eur. Pat. Appln. No. 0004949; U.S. Pat. No. 4,377,584; Eur. Pat. Appln. No. 200859; Eur. Pat. Appln. 0155096; U.S. Pat. No. 4,845,104; Eur. Pat. Appln. 0462662; Eur. Pat. Appln. 0484094 A2; U.S. Pat. No. 4,859,681; WO 91/12261; WO 94/03474; WO 94/03475; WO 94/034476.

The 17β-alkanoyl derivatives are described in J. Med. Chem. 29, 2298–2315 (1986), Eur. Pat. Appln. No. 314119, Eur. Pat. Appln. No. 367502, U.S. Pat. No. 5,061,803, Eur. Pat. Appln. No. 478066.

The invention provides compounds of the following formula (I)

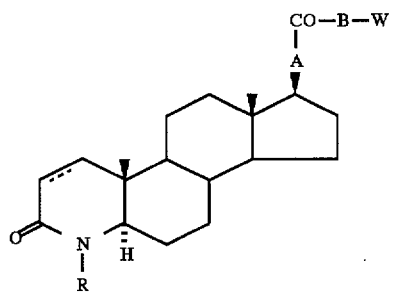

wherein the symbol --- represents a single or a double bond

R is a hydrogen atom or a $C_1$–$C_4$ alkyl group;

A is a single bond or a straight or branched $C_1$–$C_6$ alkylene chain;

B is a straight or branched $C_1$–$C_{12}$ alkylene group optionally substituted by one or more aryl groups or fluorine atoms;

W is a group $R_1$ or

wherein $R_1$ is a straight or branched $C_1$–$C_6$ alkyl group unsubstituted or substituted by one or more fluorine atoms, provided that at least one fluorine atom is present in B or W.

In the formulae of this specification the dotted line ⋯ indicates a substituent in the α-configuration, i.e. below the plane of the ring, and the wedged line ◂ indicates a substituent in the β-configuration, i.e. above the plane of the ring.

The configuration of the chiral centers in the side chain is unspecified; the invention is meant to include both the single "R" and "S" epimers as well as their "RS" mixtures.

The invention includes all the possible isomers of formula (I) and their mixture.

Also the metabolites and the metabolic precursors of the compounds of formula (I) are within the scope of the present invention.

In this specification the alkyl groups may be straight or branched chain.

A $C_1$–$C_4$ alkyl group may be, for example, methyl, ethyl, isopropyl, n-butyl or tert-butyl.

A straight or branched $C_1$–$C_6$ alkylene chain may be, for example, a straight or branched $C_1$–$C_4$ alkylene chain; in particular it may be

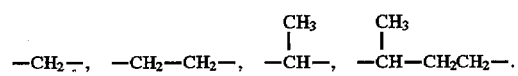

A straight or branched $C_1$–$C_{12}$ alkylene chain may be, for example, a short or medium straight chain, in particular $(CH_2)_n$ wherein n is 1, 2, 3, 4 or n is 8, 9, 10; or a mono-branched chain or a multi-branched chain, in particular, e.g.,

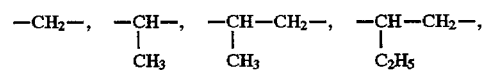

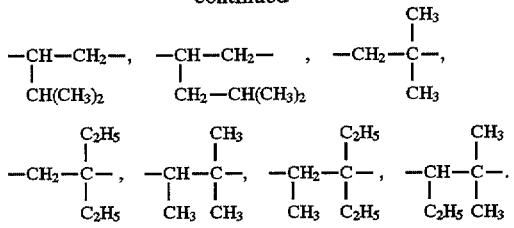

An aryl group may be, for example, phenyl, unsubstituted or substituted by, e.g., one or more, preferably one, halogen atoms, e.g., chloro, bromo or fluoro; $C_1$–$C_4$-alkyl, preferably methyl or isobutyl; $C_1$–$C_4$ alkoxy, preferably methoxy; hydroxy, or trifluoromethyl groups. A substituted phenyl group may be, e.g., in particular, 4-methylphenyl, 4-methoxyphenyl, 4-trifluoromethylphenyl, 4-fluorophenyl or 4-chlorophenyl.

A straight or branched $C_1$–$C_{12}$ alkylene chain substituted by aryl groups or fluorine atoms may be, for example, a $C_1$–$C_6$ alkylene chain substituted by an aryl group as defined above and/or one or two $CF_3$ group or one or more fluorine atoms; in particular it may be

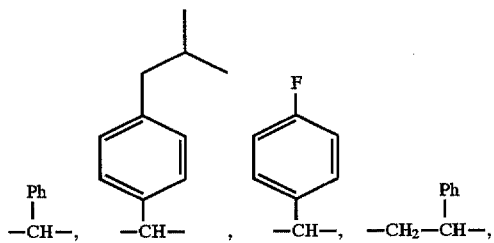

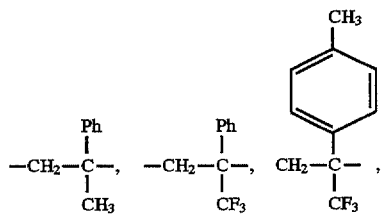

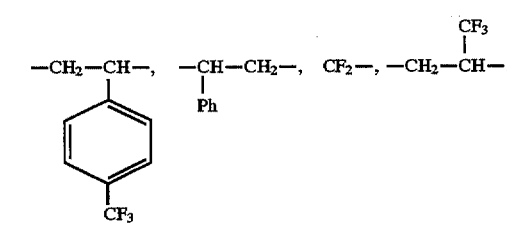

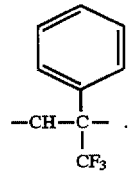

A straight or branched $C_1$–$C_6$ alkyl group may be, preferably, a $C_1$–$C_6$ straight chain alkyl, in particular methyl or butyl.

A straight or branched $C_1$–$C_6$ alkyl -group substituted by fluorine atoms may be, preferably, a straight or branched $C_1$–$C_6$ alkyl group containing, preferably, 1,2,3,5 or 7 fluorine atoms in particular fluoromethyl, difluoromethyl, trifluoromethyl, 2,2,2-trifluorol ethyl, 3,3,3-trifluoropropyl, 4,4,4-trifluorobutyl, pentafluoroethyl, eptafluoropropyl, 1,1,1,3,3,3-hexafluoroprop-2-yl or 4,4,5,5,5-pentafluoropentyl.

Preferred compounds of formula (I) are those wherein the symbol --- is a single or a double bond;

R is hydrogen or methyl;

A is a single bond or

B is:

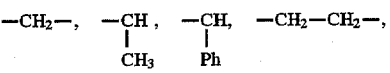

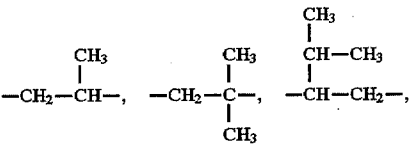

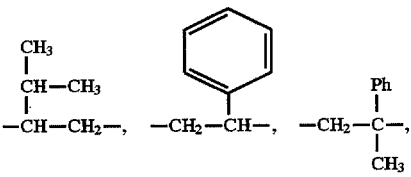

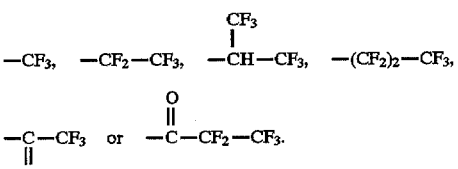

W is

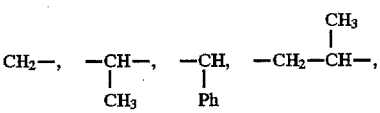

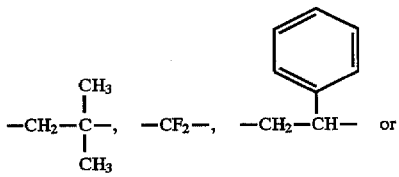

Most preferred compounds, according to the invention are the compounds of formula (I) wherein:

The symbol --- represents a single or a double bond;

R is hydrogen or methyl;

A is a single bond;

B is:

$CH_2-$, $-CH-$ with $CH_3$, $-CH-$ with $Ph$, $-CH_2-CH-$ with $CH_3$, $-CH_2-C-$ with $CH_3$/$CH_3$, $-CF_2-$, $-CH_2-CH-$ with phenyl or -continued

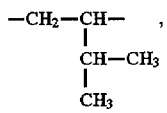

W is

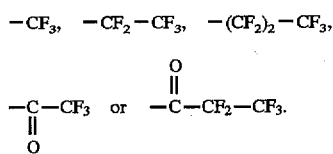

Examples of preferred compounds under this invention are:

1) 21,21-difluoro-21-heptafluoropropyl-4-aza-5α-pregn-1-en-3,20-dione; 2) 21-trifluoromethyl-4-aza-5α-pregn-1-en-3,20-dione; 3) 21-methyl-21-trifluoromethyl-4-aza-5α-pregn-1-en-3,20-dione; 4) 21-trifluoromethyl-21-phenyl-4-aza-5α-pregn-1-en-3,20-dione; 5) 21-trifluoromethyl-21-phenyl-4-aza-5α-pregnan-3,20-dione; 6) 4-methyl-21-trifluoromethyl-21-phenyl-4-aza-5α-pregn-1-en-3,20-dione;

7) 21-pentafluoroethyl-21-phenyl-4-aza-5α-pregn-1-en-3,20-dione;

8) 21-(1,1,1-trifluoroprop-2-yl)-4-aza-5α-pregn-1-en-3,20-dione;

9) 21-(1,1,1-trifluorophenylethyl)-4-aza-5α-pregn-1-en-3,20-dione;

10) 21-(1,1,1-trifluorophenylpropyl)-47aza-5α-pregn-1-en-3,20-dione;

11) 21-(1,1,1-trifluoro-2-phenylprop-2-yl)-4-aza-5α-pregn-1-en-3,20-dione;

12) 21-(1,1,1,3,3,3-hexafluoro-2-phenylpropyl)-4aza-5α-pregn-1-en-3,20-dione;

13) 21-(1,1,1-trifluoro-2-oxobut-3-yl)-4-aza-5α-pregn-1-en-3,20-dione;

14) 21-(1,1,1-trifluoro-3-methyl-2-oxobut-3-yl)-4-aza-5α-pregn-1-en-3,20-dione;

15) 21-(1,1,1-trifluoro-2-oxo-phenylpropyl)-4-aza-5α-pregn-1-en-3,20-dione and 16) 21-(1,1,1-trifluoro-4-methyl-2-oxopent-3-yl)-4-aza-5α-pregn-1-en-3,20-dione.

The above listed compounds according to their progressive number, are tabulated below with reference to the substituents as defined for formula (I).

| Cpd | R | = | A | B | W |
|---|---|---|---|---|---|
| 1 | H | double bond | single bond | $-CF_2-$ | $-CF_2CF_2CF_3$ |
| 2 | H | double bond | single bond | $-CH_2-$ | $-CF_3$ |
| 3 | H | double bond | single bond | $-CH(CH_3)-$ | $-CF_3$ |
| 4 | H | double bond | single bond | $-CH(Ph)-$ | $-CF_3$ |
| 5 | H | single bond | single bond | $-CH(Ph)-$ | $-CF_3$ |
| 6 | $CH_3$ | double bond | single bond | $-CH(Ph)-$ | $-CF_3$ |
| 7 | H | double bond | single bond | $-CH(Ph)-$ | $-CF_2CF_3$ |
| 8 | H | double bond | single bond | $-CH_2-CH(CH_3)-$ | $-CF_3$ |
| 9 | H | double bond | single bond | $-CH_2-CH(Ph)-$ | $-CF_3$ |
| 10 | H | double bond | single bond | $-CH_2-CH(Ph)-$ | $-CF_2CF_3$ |
| 11 | H | double bond | single bond | $-CH_2-C(CH_3)(Ph)-$ | $-CF_3$ |
| 12 | H | double bond | single bond | $-CH_2-C(CF_3)(Ph)-$ | $-CF_3$ |

-continued

| Cpd | R | = | A | B | W |
|---|---|---|---|---|---|
| 13 | H | double bond | single bond | —CH$_2$—CH—<br>\|<br>CH$_3$ | —COCF$_3$ |
| 14 | H | double bond | single bond | CH$_3$<br>\|<br>—CH$_2$—C—<br>\|<br>CH$_3$ | —COCF$_3$ |
| 15 | H | double bond | single bond | —CH$_2$—CH—<br>\|<br>Ph | —COCF$_3$ |
| 16 | H | double bond | single bond | —CH$_2$—CH—<br>\|<br>CH<br>/ \<br>CH$_3$  CH$_3$ | —COCF$_3$ |

The compounds of formula (I) may be obtained by a process comprising:

a) reacting a compound of formula (II)

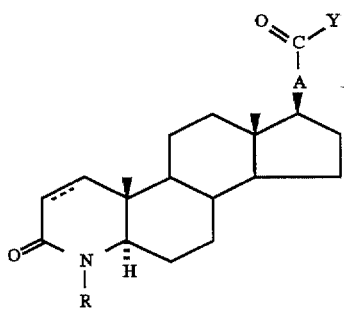

wherein the symbol ---, R, A are as defined above and Y is an activating group of the carboxylic function, with organometallic compound of formula (III)

(Hal)$_n$M-B-R$_1$    (III)

wherein M is a metal atom, Hal is a halogen atom, R$_1$ is as defined above and n is zero, 1 or 2, so obtaining a compound of formula (I), wherein the symbol ---, R, A and B are as defined above and W is a group R$_1$ as defined above; or b) reducing a compound of formula (IV)

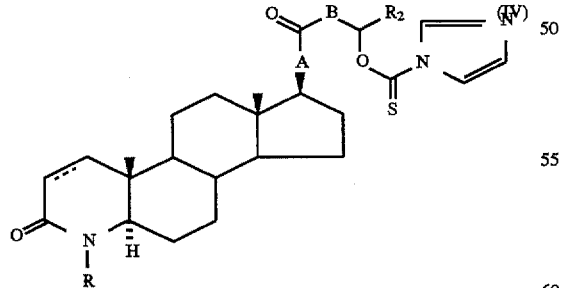

wherein the symbol ---, R, A, and B are as defined above and R$_2$ is a straight or branched C$_1$-C$_5$ alkyl group, so obtaining a compound of formula (I), wherein the symbol ---, R, B are as defined above and W is a group R$_1$ as defined above provided that, in this case, R$_1$ has only the meanings corresponding to CH$_2$—R$_2$ wherein R$_2$ is as defined hereabove; or c) oxidizing a compound of formula (V)

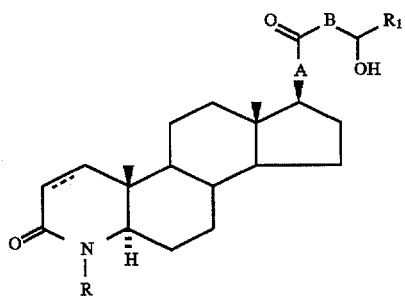

wherein the symbol ---, R, A, B and R$_1$ are as defined above, so obtaining a compound of formula (I), wherein the symbol ---, R, A, and B are as defined above and W is a group —C-R1 as defined above; or d) deprotecting a compound of formula (VI)

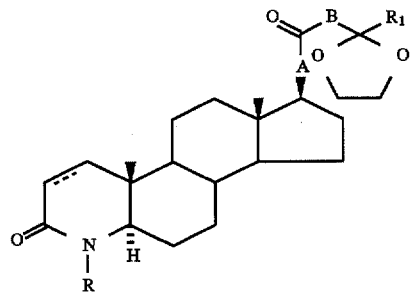

wherein ---, R, A, B and R$_1$ are as defined above, so obtaining a compound of formula (I), wherein R, A and B are as defined above and W is a group

—C—R$_1$,
‖
O wherein R$_1$ is as defined above; and, if desired, e) dehydrogenating a compound of formula (I), wherein the symbol --- is a single bond, R, A, B and W are as defined above, so obtaining a compound of formula (I), wherein the symbol --- is a double bond, R, A, B, W are as defined above and/or, if desired, separating a mixture of isomers of formula (I) into the single isomers.

The activating group Y of the carboxylic function, in the compound of formula (II) is preferably one of the following groups:

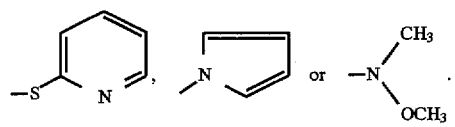

The metal atom M in the compound of formula (III) is, in particular, an alkali or alkaline earth metal atom, such as, for example Li, Mg or Cd.

The halogen atom Hal in the compound of formula (III) is, preferably, chlorine, bromine or iodine.

The reaction of a compound of formula (II) with a compound of formula (III), according to the reaction variant a) may be carried out treating the compound of formula (II) with the organometallic reagent of formula (III), preferably an organomagnesium compound (Grignard reagent) or an organolithium compound, in an anhydrous solvent such as, for example, diethyl ether, tetrahydrofurane (THF), at a temperature ranging from about −78° C. to about −30° C. for a time varying, e.g., from about one hour to about four hours, under an inert atmosphere of, for example, nitrogen or argon. The reduction of a compound of formula (IV) to obtain a compound of formula (I), according to the reaction variant b), may be carried out treating a compound of formula (IV) with tri-n-butyltin hydride, sometimes in the presence of azobisisobutyronitrile (AIBN) as radical initiator, in a solvent such as, for example, toluene, at a temperature ranging, e.g., from the room temperature to the reflux temperature of the reaction mixture, for a time varying, e.g., from one to four hours.

The oxidation of a compound of formula (V) to obtain a compound of formula (I), according to the reaction variant c) may be carried out by the Swern reagent (Synthesis 1981, 165) or by the Dess-Martin reagent (Tetr. Lett. 1987, 28, 4259), in the usual conditions well known to those skilled in the art.

The deprotection of a compound of formula (VI) according to the reaction variant d), may be carried out by treatment of a compound of formula (VI) in an alcoholic solvent such as, for example, methanol or ethanol, with concentrated halogenidric acid, such as, for example, hydrochloric or hydrobromic acid, at a temperature varying from room temperature to the reflux temperature of the reaction mixture, for a time of about some hours to 48 hours.

The dehydrogenation of a compound of formula (I) according to the process variant e), may be carried out with a dehydrogenating agent, e.g. benzeneseleninic anhydride or DDQ, in an anhydrous solvent such as, for example, chlorobenzene, dioxane, xylene, toluene, benzene, optionally in the presence of bis(trimethylsilyl)trifluoroacetamide (BSTFA) (especially when DDQ is used), at a temperature ranging from room temperature to the reflux temperature of the solvent, for a time varying from about two hours to about 24 hours, preferably in an inert atmosphere of nitrogen.

Standard procedures may be used for separating a mixture of isomers of formula (I) into single isomers.

A compound of formula (IV), may be obtained reacting a compound of formula (v), wherein the symbol ---, R, A, B, R₁ are as defined above, with a compound of formula (VII)

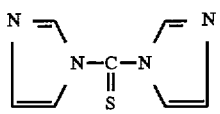

The reaction is performed refluxing a mixture of the alcohol of formula (V) and excess 1,1-thiocarbonyldiimidazole of formula (VII) in an anhydrous solvent such as, for example, 1,2-dichloroethane, methylene chloride, tetrahydrofurane, for a time varying from about 1 hour to about 8 hours preferably under an inert atmosphere of, for example, nitrogen.

A compound of formula (V), may be obtained, e.g., deprotecting a compound of formula (VIII)

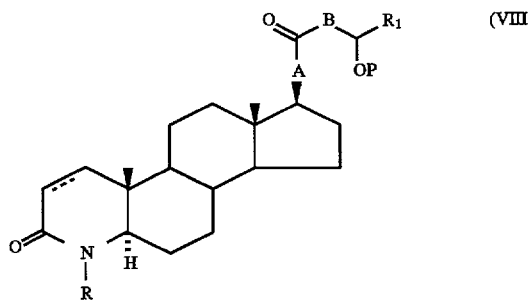

wherein the symbol ---, R, A, B and R₁ are as defined above and P is a suitable protecting group of the hydroxy group, such as, for example, a tetrahydropyranyl group or a trialkylsilyl group e.g. a trimethylsilyl or tertbutyldimethylsilyl group.

The reaction is carried out in the usual conditions used for removing tetrahydropiranyl groups or silyl groups (see, for example, Greene T. W.; Wutz P. G., Protective groups in Organic Synthesis, 2nd ed.; Wiley; New York 1991).

A compound of formula (VIII) may be obtained reacting a compound of formula (II), wherein the symbol ---, R, A and Y are as defined above, with a compound of formula (IX)

wherein B, P and R₁ are as defined above and Hal, M and n are as defined for a compound of formula (III).

The reaction may be carried out treating the compound of formula (II) with the organometallic reagent of formula (IX), preferably an organomagnesium compound (Grignard reagent) or an organolithium compound, in an anhydrous solvent such as, for example, diethyl ether, tetrahydrofurane (THF), at a temperature ranging, e.g., from about −78° C. to about −30° C., for a time varying, e.g., from about 1 hour to about four hours, under an inhert atmosphere of, for example, nitrogen or argon.

A compound of formula (VI), may be obtained reacting a compound of formula (II) with a compound of formula (X)

wherein B and R₁ are as defined above and Hal, M and n are as defined for compounds of formula (III).

The reaction may be carried out in the same conditions hereabove reported for the reaction between compounds (IX) and compounds (II).

The compounds of formula (II), (III), (VII), (IX) and (X) are known compounds or they may be synthesized by known methods as described in the literature.

Alternatively, the compounds of formula (I) wherein B has the particular meaning

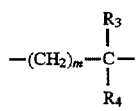

in which m is 0 or 1, $R_3$ is hydrogen or aryl and $R_4$ is a $C_1$–$C_{11}$ alkyl group optionally substituted by one or more aryl groups or fluorine atoms; A is a single bond, R, W and --- are as defined above, may be obtained according to the scheme reported here below.

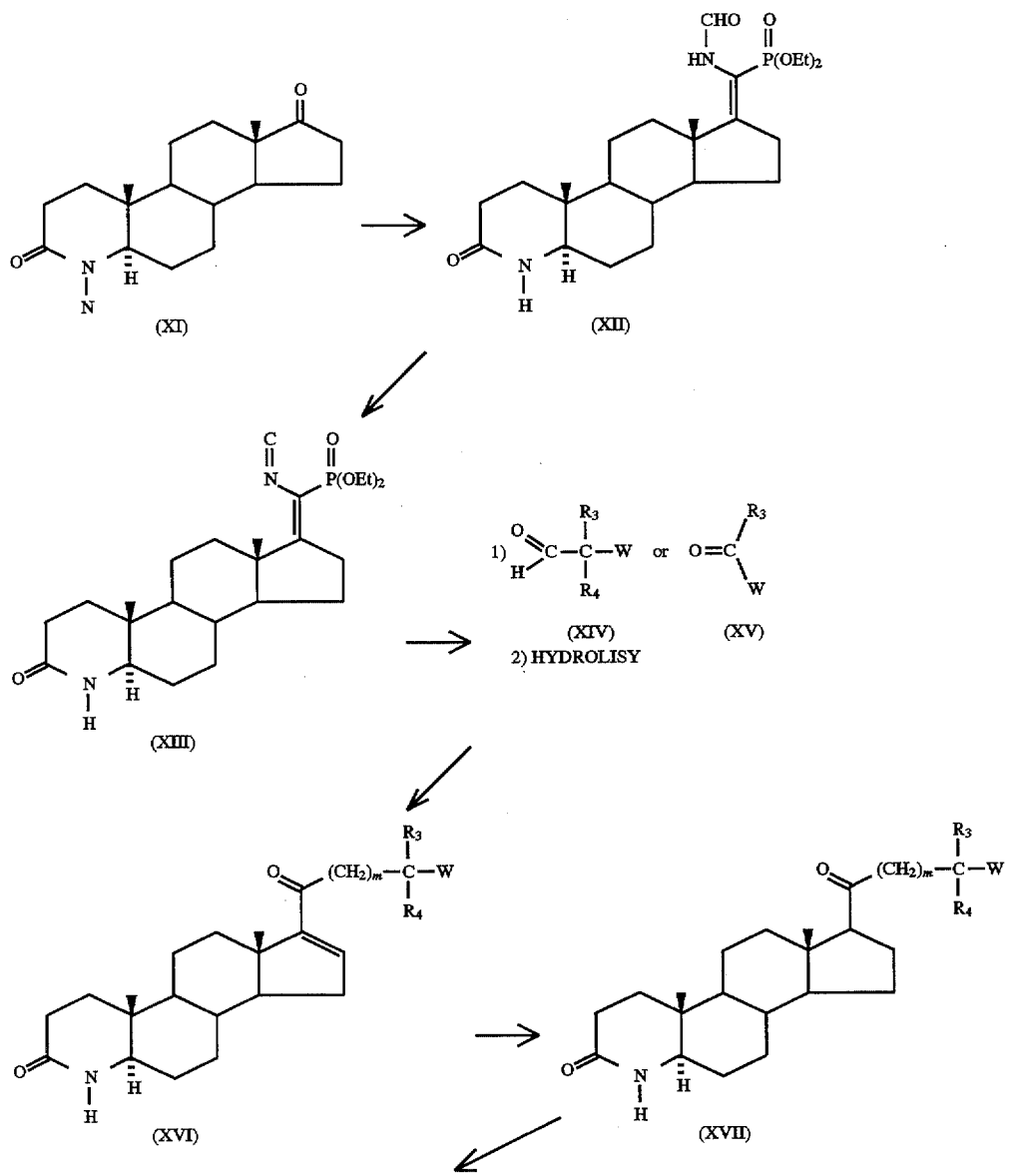

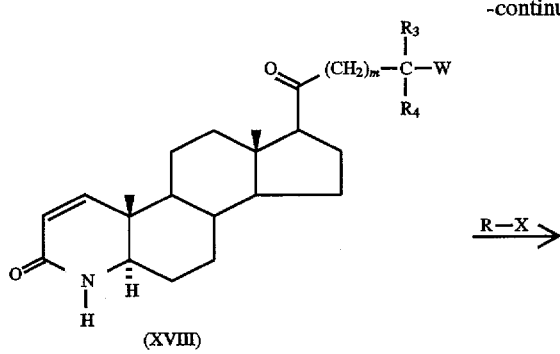
(XVIII)

R—X →

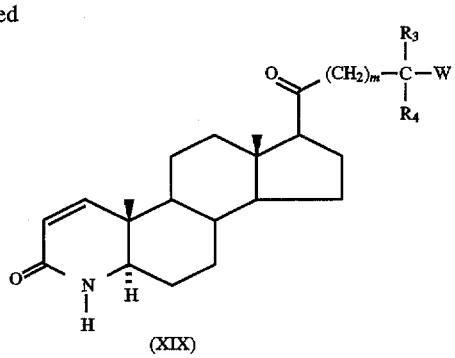
(XIX)

According to the above reported scheme 4-aza-5α-androstan-3,17-dione of formula (XI) undergoes a formal Knoevenagel condensation with diethyl (isocyanomethyl) fosfanate, according to what reported in J.O.C. 57, 2249–2252 (1992), to yield the compound of formula (XII) which, in its turn, is dehydrated, in the standard conditions (Synthesis 400, 1985) to afford the (E)-17-[(diethylphosphono)isocyanomethylene]-4-aza-steroid of formula (XIII).

The compound of formula (XIII) undergoes, a Wittig-Horner-Emmons reaction with an aldehyde or a ketone of formula (XIV) or (XV) wherein $R_3$ and $R_4$ and W are as defined above.

In particular when W is

the carbonyl group may be in a protected form, or may be reduced to alcohol and suitably protected, according to the strategy required by the synthetic pathway. The reaction is carried out according to what reported in the literature (e.g. J.O.C. 58, 3687–91 (1993) to afford α,β-unsaturated isocyanides which after acidic hydrolisis give $\Delta^{16-20}$-4-azasteroids of formula (XVI).

Reduction of the 16–17 double bond by catalytic hydrogenation on 10% Pd/C in ethanol under hydrogen pressure (40–50 psi) affords compounds of formula (XVII), that is compounds of formula (I) wherein B is

and W is $R_4$.

Compounds of formula (XVII) may be optionally unsaturated at the 1,2-position by phenylselenic anhydride (standard method for 4-azasteroids) and, optionally may be alkylated on the 4-nitrogen by an alkyl halide of formula RX, wherein R is as defined above and X is an halogen atom, preferably I, Br or Cl, to obtain a compound of formula (XIX).

The compounds of formula (XIV) and (XV) are known compounds. The compounds of formula (I) of the present invention inhibit specifically the testosterone 5α-reductase enzyme and, therefore, are potent anti-androgens.

For example, the inhibitory effect of the compounds of the invention on 5α-reductase was determined in vitro according to the procedure reported herebelow.

In Vitro Assay of 5α-reductase Inhibition

Inhibition of 5α-reductase was evaluated using the particulate fraction from homogenates of hyperplastic human prostates as the enzyme source. The particulate fraction was prepared centrifuging prostate homogenate at 140,000×g. The resulting pellet, washed several times, was resuspended in buffer and stored at −80° C. in aliquots containing ≈10 mg protein/ml.

The assay for 5α-reductase was done in a final volume of 0.5 ml, in 40 mM TRIS-HCl buffer pH 5.5, containing 1 mM dithiothreitol, 5 mM NADPH, 1 mM [$^{14}$C]testosterone, an aliquot of the enzyme preparation and various concentrations of the inhibitors. After 30 min incubation at 37° C. the reaction was terminated by addition of 2 ml cold diethyl ether and the organic phase was separated, evaporated under $N_2$ and resuspended in ethyl acetate.

Testosterone metabolites in this extract were separated in TLC on silica gel F 254 plates (Merck), using chloroform, acetone and n-hexane (2:1:2) as developing solvent system. Radioactivity on the plate was scanned and analysed from quantitative plots printed by a TLC-analyzer (Berthold). The fractional 5α-reduction of testosterone was calculated by relating the $^{14}$C-radioactivity in the 5α-reduced metabolites (5α-dihydrotestosterone, 3α- and 3β- androstanediols) regions to the total radioactivity in the testosterone and 5α-reduced metabolites regions.

The concentration of each compound required to reduce control 5α-reductase activity by 50% ($IC_{50}$) was determined by plotting % inhibition versus log for inhibitor concentration.

In view of the activity shown in the above test procedure the compounds of the invention can be therapeutically useful in the situations in which a decrease in androgen action, by means of 5α-reductase inhibition, is desirable such as, for example, benign prostatic hyperplasia, prostatic and breast cancers, and certain skin-hair conditions such as, e.g., acne, seborrhoea, female hirsutism and male pattern baldness. A mammal, human or animal, may thus be treated by a method which comprises administering thereto a pharmaceutically effective amount of a compound of formula (I) or a pharmaceutically acceptable salt thereof as defined above.

The toxicity of the compounds of the invention is quite negligible so that they can be safely used in therapy. The compounds of the invention can be administered in a variety of dosage forms, e.g. orally, in the form of tablets, capsules, sugar- or film-coated tablets, liquid solutions or suspensions; rectally, in the form of suppositories; parenterally, e.g. intra-muscularly, or by intravenous injection or infusion; or topically, e.g. in the form of creams.

The dosage depends on the age, weight, conditions of the patient and administration route; for example, the dosage adopted for oral administration to adult humans may range from about 1 to 200 mg pro dose, from 1 to 3 times daily.

As already said, the invention includes pharmaceutical compositions comprising a compound of the invention in association with a pharmaceutically acceptable excipient (which can be a carrier or diluent).

The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate; effervescing mixtures; dye-stuffs; sweeteners; wetting agents, such as lecithin, polysorbates, laurylsulphates; and, in general non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions, for oral administration may be, e.g. syrups, emulsions and suspensions.

The syrups may contain as carrier, for example, saccharose with glycerine and/or mannitol and/or sorbitol; in particular a syrup to be administered to diabetic patients can contain as carriers only products not metabolizable to glucose, or metabolizable in very small amount to glucose, for example, sorbitol.

The suspensions and the emulsions may contain as carrier, for example, a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycol, e.g. propylene glycol and if desired, a suitable amount of lidocaine hydrochloride.

The solutions for intravenous injections or infusions may contain as carrier, for example, sterile water or preferably they may be in the form of sterile, aqueous, isotonic saline solutions.

The suppositories may contain together with the active compound a pharmaceutically acceptable carrier, e.g. cocoabutter, polyethylene glycol, a polyoxyethylene sorbitan fatty acid ester surfactant or lecithin.

Conventional carriers may be used for topical formulations.

The present invention further provides a compound of formula (I), or a pharmaceutically acceptable salt thereof, for use in a method of treatment of the human or animal body by therapy in particular for use as a testosterone 5α-reductase inhibitor.

The present invention further provides the use of a compound of formula (I) or a pharmaceutically acceptable salt thereof in the manufacture of a medicament for use as a testosterone 5α-reductase inhibitor.

The following examples further illustrate the invention. The reported NMR data are determined in $CDCl_3$.

EXAMPLE 1

21,21-difluoro-21-heptafluoropropyl-4-aza-5α-pregn-1-en-3,20-dione (Compound (I): R=H, ---=double bond, B=single bond, B=$CF_2$, W=$CF_2CF_2CF_3$).

To a 25% solution of phenylmagnesium bromide in THF (>>1.42M) (5 ml) cooled to −50° C. with a dry-ice bath, a solution of perfluorobutyliodide (2.076 g=1.01 ml) in anhydrous tetrahydrofurane (6.0 ml) was added dropwise.

While the temperature was maintained at −78° C., S-(2-Pyridyl) 3-oxo-4-aza-5α-androst-1-ene-17β-carbothioate (410mg) dissolved in anhydrous tetrahydrofurane (20 ml) was added and the mixture was stirred at −78° C. for 1 h and then the temperature was allowed to rise to 0° C. Saturated sodium chloride solution was added dropwise; the inorganic salt that separated was filtered off, washed with diethyl ether and the filtrates were evaporated to a residue. The residue dissolved in methylene chloride was washed with 10% sodium hydroxyde, saturated sodium chloride solution, dried and concentrated. The crude oil so obtained was purified by flash chromatography (eluant: methylene chloride/acetone 9:1) so obtaining 150 mg of the title compound.

Following an analogous procedure the compounds listed below are prepared:

21-trifluoromethyl-4-aza-5α-pregn-1-en-3,20-dione;

21-methyl-21-trifluoromethyl-4-aza-5α-pregn-1-en-3,20-dione and 21-trifluoromethyl-21-phenyl-4-aza-5α-pregn-1-en-3,20-dione.

EXAMPLE 2

21-(1,1,1-trifluoro-2-oxobut-3-yl)-4-aza-5α-pregn-1-en-3,20-dione (Compound (I): R=H, ---=double bond, A=single bond, B=—$CH_2CH(CH_3)$—, W=—$COCF_3$)

The Grignard reagent was prepared adding a solution of 3-ethylendioxo-4,4,4-trifluoro-2-methylbutylbromide (1.242 g) in anhydrous tetrahydrofurane (10 ml) to magnesium turnings (146 mg) in anhydrous tetrahydrofurane (10 ml) at 30–35° C.

The stirring was continued for 1 h and then the solution was added dropwise to a stirred solution of S-(2-Pyridyl)3-oxo-4-aza-5α-androst-1-en-17β-carbothloate (410 mg) in anhydrous tetrahydrofurane (20 ml), maintained at −78° C. After 1 h the temperature was allowed to rise to 0° C., saturated ammonium chloride was added dropwise and the stirring was continued for 1 h at room temperature. The precipitate was removed by filtration and the filtrates were concentrated to a residue; the residue was dissolved in methylene chloride, washed with 10% sodium hydroxide, saturated sodium chloride and dried.

The solvent was evaporated under vacuum and the crude oil so obtained was purified by flash chromatography (eluant methylene chloride/ethyl acetate 80:20) to afford 150 mg of 17β-(3,3-ethylendioxo-4,4,4-trifluoro-2-methylbutylcarbonyl)-4-aza-5α-androst-1-en-3-one.

A solution of the ketal (150 mg) in methanol (2 ml) was treated with 37% hydrochloric acid (0.5 ml) and the mixture was heated at reflux for 8 hrs. After cooling the reaction mixture was poured into ice-water (50 ml) and extracted with ethyl acetate; the combined organic extracts were washed with saturated sodium hydrogencarbonate solution, brine, and dried over sodium sulphate.

After evaporation of the solvent under vacuum, the crude residue was purified by flash chromatography on silica gel (eluant methylene chloride/acetone 90:10) to yield 80 mg of the title compound.

Following an analogous procedure the compound listed below are prepared:

21-(1,1,1-trifluoro-3-methyl-2-oxobut-3-yl)-4-aza-5α-pregn-1-en-3,20-dione;

21-(1,1,1-trifluoro-2-oxo-phenylpropyl)-4-aza-5α-pregn-1-en-3,20-dione and 21-(1,1,1-trifluoro-4-methyl-2-oxopent-3-yl)-4-aza-5α-pregn-1-en-3,20-dione.

EXAMPLE 3

(21R,S)-21-trifluoromethyl-21-phenyl-4-aza-5α-pregnan-3,20-dione (Compound (I): ---=single bond, A=single bond, R=H,

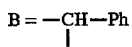

W=CF$_3$, that is compound XVII, wherein R$_3$=—Ph, R$_4$=CF$_3$)

Potassium tert-butylate (4.49 g) is added, at room temperature, to a well stirred solution of 4-aza-5α-androstan-3,17-dione (2.854 g) in methylene chloride (80 ml), under nitrogen atmosphere. The mixture is immediately cooled to −15° C. and, after stirring at this temperature for 20 minutes, neat diethyl(isocyanomethyl)phosphonate (1.9 ml) is added dropwise. The temperature is slowly raised to 0° C. and stirring is continued at this temperature for 1.5 h. Water (100 ml) and methylene chloride (200 ml) are added and the organic layer is separated, washed with water until neutral and dried over sodium sulphate. The solvent is removed under vacuum and the crude product (5.3 g) is purified by flash chromatography on silica gel (eluant: methylene chloride/ethyl acetate/methanol 50:40:10) to yield 3.14 g of (E)-17-[(diethylphosphono)formaraidomethylene]-4-aza-5α-pregnan-3-one [Compound XII].

NMR (CDCl$_3$) δ:0.8 (s, 3H, CH$_3$(18)), 1 (s, 3H, H(19)), 1.2–1.4 (m, 6H, OCH$_2$CH$_3$), 4.2 (m, 4H, OCH$_2$CH$_3$), 5.8 (d, 1H, NH), 6.6–6.8 (m, 1H, NHCHO), 7.8–8.2 (s, 1H, CHO).

To a stirred solution of (E)-17-[(diethylphosphono)formaraidomethylene]-4-aza-5α-pregnan-3-one (1.10 g) in tetrahydrofurane (14 ml) at −30° C. in a nitrogen atmosphere, were added subsequently diisopropylaraine (0.91 ml) and phosphorus oxychloride (0.43 ml). After stirring at −30° C. for 1.75 h, a saturated aqueous sodium carbonate solution (10 ml) was added. After addition of water (100 ml), extraction with methylene chloride (2×100 ml), drying of the combined extracts over sodium sulphate and evaporation of the solvent, 925 mg of crude material were obtained. Further purification by flash chromatography on silica gel (eluant: methylene chloride/ethyl acetate/methanol 50:35:15) afford 825 mg of (E)-17-[(diethylphosphono)isocyanomethylene]-4-aza-5α-pregnan-3-one [Compound XIII].

NMR (CDCl$_3$) δ:0.8 (s, CH$_3$(18)), 1.0 (s, 3H, CH$_3$(19)), 1.3–1.6 (t, 6H, OCH$_2$CH$_3$), 4.0–4.4 (q, 4H, OCH$_2$CH$_3$), 5.8 (s, 1H, NH).

A solution of (E)-17-[(diethylphosphono)isocyanomethylene]-4-aza-5α-pregnan-3-one (500 mg) in anhydrous tetrahydrofurane (28 ml) is treated, at −30° C., with potassium tert-butylate (276 mg). After stirring at −30° C. for ten minutes, trifluoroaceto-phenone (0.46 ml) is added and stirring is continued for 30 min. at −20° C. Then the reaction is allowed to reach 0° C. and water is added. The mixture is extracted with ethyl ether and the combined extracts are washed with water until neutral. The solvent is evaporated under vacuum and the crude material is purified by flash chromatography on silica gel (eluant: benzene/ethyl acetate/methanol 70:20:5) to afford 20-isocyano-21-trifluoromethyl-21-phenyl-4-aza-5α-pregn-20-en-3-one.

NMR (CDCl$_3$) δ:0.9 (s, 3H, CH$_3$(18)), 1.0 (s, 3H, CH$_3$(19)), 3.0 (m, 1H, H(5α)), 5,4 (m, 1H, H(16)), 5.5 (bs, 1H, NH(4)).

MS(FAB$^+$) m/z: 469 (M+1).

To a stirred solution of (21R,S)-20-isocyano-21-trifluoro-21-phenyl-4-aza-5α-pregn-20-en-3-one (127 mg) in tetrahydrofurane (6.0 ml) 20% aqueous sulphure acid (0.5 ml) is added. The mixture is refluxed for 2 hrs., after which a saturated aqueous sodium carbonate solution is added. Then the solution is diluted with water and extracted with methylene chloride. The organic extracts are washed with water until neutral and dried over sodium sulphate. The solvent is removed under vacuum and the crude is purified by flash chromatography on silica gel (eluant: methylene chloride/acetone 70:30) to yield (21R,S)-21-trifluoromethyl-21-phenyl-4-aza-5α-pregn-16-en-3,20-dione (92 mg) [Compound XVI wherein R$_3$=Ph, R$_4$=CF$_3$].

NMR (CDCl$_3$) δ:0.9 (s, 3H, CH$_3$(19)), 1.4 (s, 3H, CH$_3$(18)), 3.0 (m, 1H, H(5α)), 4.8 (q, 1H, CH(CF$_3$)Ph), 5.5 (bs, 1H, NH(4)), 6.6, (m, 1H, H(16)), 7.3 (m, 5H, Ph).

MS(FAB$^+$) m/z: 460 (M+1).

A solution of (21R,S)-21-trifluoromethyl-21-phenyl-4-aza-5α-pregn-16-en-3,20-dione (73 mg) in ethanol (5.0 ml) is hydrogenated under hydrogen pressure (40–50 psi), on 10% Palladium on charcoal (30 mg) in a Parr apparatus for about 2 hrs. at room temperature. The catalyst is removed by filtration, the solvent is evaporated under vacuum and the solid residue is chromatographed on silica gel (eluant: methylene chloride/acetone 80:20) to yield the title compound (52 mg).

NMR (CDCl$_3$) δ:0.83 (s, 3H, CH$_3$(18)), 0.90 (s, 3H, CH$_3$(19)), 3.0 (m, 1H, H(5α) ), 4.8 (q, 1H, CH(CF$_3$)Ph), 5.5 (bs, 1H, NH(4)), 7.3 (m, 5H, Ph).

EXAMPLE 4

(21R, S)-21-trifluoromethyl-21-phenyl-4-aza-5α-pregn-16-en-3,20-dione (Compound (I): ---=double bond, A=single bond, R=H,

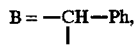

W=CF$_3$, that is compound XVIII, wherein R$_3$=—Ph, R$_4$=CF$_3$)

A mixture of (21R, S)-21-trifluoromethyl-21-phenyl-aza-5α-pregnan-3,20-dione (74 mg) and benzeneselenic anhydride (160 mg) in chlorobenzene (4.0 ml) are refluxed for 4 hrs. The solvent is removed under vacuum and the crude is dissolved in CH$_2$Cl$_2$ (20 ml) and washed with saturated sodium chloride solution and dried over sodium sulphate. The solvent is evaporated under vacuum and the yellowish residue is purified by flash chromatography on silica gel (eluant: methylene chloride/acetone 80:20) to yield 38 mg of the title compound as a solid foam.

NMR (CDCl$_3$) δ:0.83 (s, 3H, CH$_3$(18)), 0.96 (s, 3H, CH$_3$(19)); 3.3 (m, 1H, H(5α)), 4.8 (q, 1H, CH(CF$_3$)Ph) , 5.5 (bs, 1H, NH(4)), 5.8 (dd, 1H, H(2)), 6.8 (d, 1H, H(1)), 7.3 (m, 5H, Ph).

Following an analogous procedure the compounds that are listed below are prepared:

21-methyl-21-trifluoromethyl-4-aza-5α-pregn-1-en-3,20-dione;

21-pentafluoroethyl-21-phenyl-4-aza-5α-pregn-1-en-3,20-dione;

21-(1,1,1-trifluoroprop-2-yl)-4-aza-5α-pregn-1-en-3,20-dione;

21-(1,1,1-trifluorophenylethyl)-4-aza-5α-pregn-1-en-3,20-dione;

21-(1,1,1,2,2-pentafluorophenylpropyl)-4-aza-5α-pregn-1-en-3,20-dione;

21-(1,1,1-trifluoro-2-phenylprop-2-yl)-4-aza-5α-pregn-1-en-3,20-dione and 21-(1,1,1,3,3,3-hexafluoro-2-phenylpropyl)-4-aza-5α-pregn-1-en-3,20-dione.

EXAMPLE 5

(21R,S)-4-methyl-21-trifluoromethyl-21-phenyl-4-aza-5α-pregn-1-en-3,20-dione (Compound (I): ---=double bond, A=single bond, R=CH$_3$, B = —CH—Ph, W=CF$_3$, that is compound XIX, wherein R$_3$=Ph, R$_4$=CF$_3$, R=CH$_3$)

To a solution of (21R, S)-21-trifluoromethyl-21-phenyl-4-aza-5α-pregn-1-en-3,20-dione (30 mg) in anhydrous dimethylformamide (2.0 ml), sodium hydride (80% suspension in mineral oil) (3.0 mg) is added and the mixture is stirred at room temperature for 15 min. Methyl iodide (6.0 μl) is added and the mixture is stirred at 40° C. for 2 hrs. After cooling the reaction mixture is diluted with water (30 ml) and extracted with methylene chloride. The combined extracts are washed with water until neutral, dried over sodium sulphate and the solvent is removed under vacuum. The crude solid that is obtained is purified by flash chromatography on silica gel (eluant: methylene chloride/acetone 90:10) to yield 21 mg of the title compound.

NMR (CDCl$_3$) δ:0.83 (s, 3H, CH$_3$(18)), 0.90 (s, 3H, CH$_3$(19)), 2.9 (s, 3H, N—CH3), 3.3 (dd, 1H, H(5α)), 4.8 (q, 1H, CH(CF$_3$)Ph), 5.8 (dd, 1H, H(2)), 6.7 (d, 1H, H(1)).

EXAMPLE 6

Scored tablets for oral use, each containing 250 mg of the active substance, were manufactured as follows.

Composition (for 10,000 tablets):

| 21-trifluoromethyl-21-phenyl-4-aza-5α-pregn-1-en-3,20-dione | 2500 g |
|---|---|
| Corn starch | 275 g |
| Talc powder | 187 g |
| Calcium stearate | 38 g |

The active substance was granulated with a 4% w/v aqueous solution of methyl cellulose. To the dried granules a mixture of the remainder of the ingredients is added and the final mixture compressed into tablets of proper weight.

EXAMPLE 7

Two-piece hard gelatin capsules for oral use, each containing 250 mg of active substance were manufactured as follows.

Compositions for 10,000 capsules:

| 21-trifluoromethyl-21-phenyl-4-aza-5α-pregn-1-en-3,20-dione | 2500 g |
|---|---|
| Lactose | 1000 g |
| Corn starch | 300 g |
| Talc powder | 65 g |
| Calcium stearate | 35 g |

The active substance was mixed with the starch-lactose mixture followed by the talc and calcium stearate.

We claim:

1. A compound of formula (I)

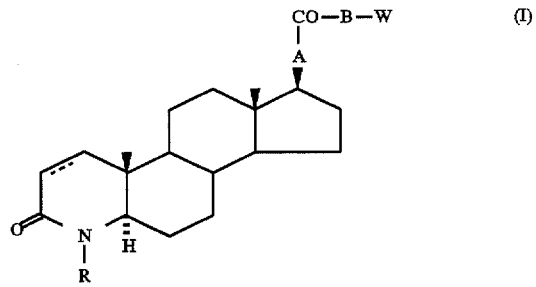

wherein the symbol --- represents a single or a double bond;

R is a hydrogen atom or a C$_1$–C$_4$ alkyl group;

A is a single bond or a straight or branched C$_1$–C$_6$ alkylene chain;

B is a straight or branched C$_1$–C12 alkylene group optionally substituted by one or more aryl groups or fluorine atoms;

W is a group

wherein R$_1$ is a straight or branched C$_1$–C$_6$ alkyl group unsubstituted or substituted by one or more fluorine atoms, provided that at least one fluorine atom is present in B or W.

2. A compound of formula (I), according to claim 1, wherein:

the symbol --- is a single or double bond;

R is hydrogen or methyl;

A is a single bond or

B is:

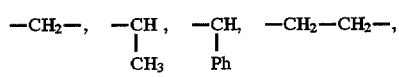

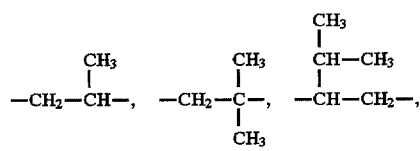

21
-continued

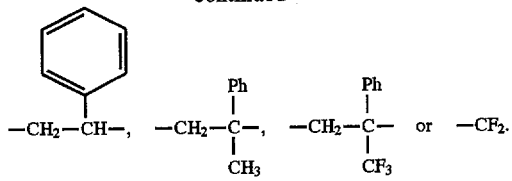

W is

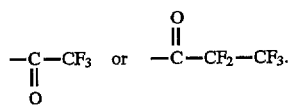

3. A compound of formula (I), according to claim 1, wherein:

the symbol --- represents a double bond;

R is hydrogen or methyl;

A is a single bond;

B is:

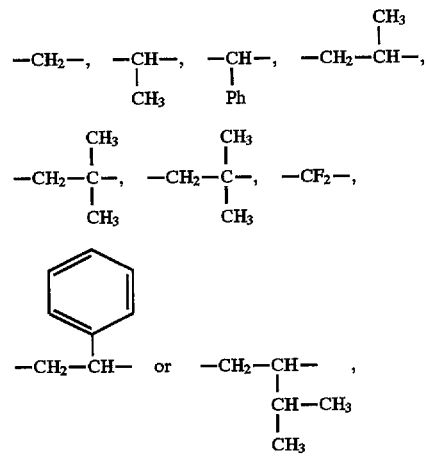

W is

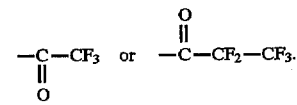

4. A pharmaceutical composition comprising a compound of formula (I), according to claim 1, as an active principle, and a pharmaceutically acceptable diluent and/or carrier.

5. A method of inhibiting 5α-reductase in a patient in need of it comprising administering to the said patient an effective amount of a compound of formula (I) according to claim 1.

6. A process for preparing a compound of formula (I), according to claim 1, comprising:

22 a) oxidizing a compound of formula (V)

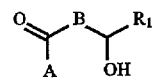

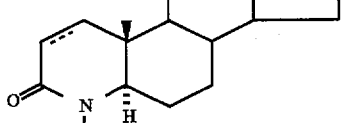

wherein the symbol ---, R, A, B and $R_1$ are as defined in claim 1 so obtaining a compound of formula (I), wherein the symbol ---, R, A, and B are as defined in claim 1 and W is a group

as defined in claim 1; or b) deprotecting a compound of formula (VI)

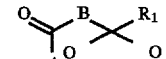

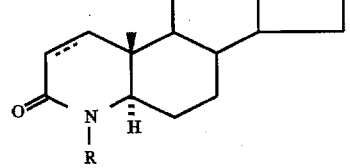

wherein ---, R, A, B and $R_1$ are as defined in claim 1, so obtaining a compound of formula (I), wherein X, R, A, and B are as defined in claim 1 and W is a group

wherein $R_1$ is as defined in claim 1; and, if desired, c) dehydrogenating a compound of formula (I) wherein the symbol --- is a single bond R, B and W are as defined in claim 1 so obtaining a compound of formula (I) wherein the symbol --- is a double bond, R, A, B and W are as defined in claim 1 and/or, if desired, separating a mixture of isomers of formula (I) into the single isomers.

7. A compound selected from the group consisting of:

21-(1,1,1-trifluoro-2-oxobut-3-yl)-4-aza-5α-pregn-1-en-3,20-dione;

21-(1,1,1-trifluoro-3-methyl-2-oxobut-3-yl)-4-aza-5α-pregn-1-en-3,20-dione;

21-(1,1,1-trifluoro-2-oxo-phenylpropyl)-4-aza-5α-pregn-1-en-3,20-dione and 21-(1,1,1-trifluoro-4-methyl-2-oxopent-3-yl)-4-aza-5α-pregn-1-en-3,20-dione.

* * * * *